United States Patent
Bartenbach et al.

(10) Patent No.: US 7,794,513 B2
(45) Date of Patent: Sep. 14, 2010

(54) PROCESS FOR THE SCALE-UP OF A REACTOR FOR CARRYING OUT A HIGH-TEMPERATURE REACTION, REACTOR AND USE

(75) Inventors: Bernd Bartenbach, Limburgerhof (DE); Kai Rainer Ehrhardt, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 1728 days.

(21) Appl. No.: 10/806,232

(22) Filed: Mar. 23, 2004

(65) Prior Publication Data

US 2004/0205996 A1 Oct. 21, 2004

(30) Foreign Application Priority Data

Mar. 26, 2003 (DE) .................. 103 13 528

(51) Int. Cl.
*C07C 11/24* (2006.01)
(52) U.S. Cl. ............................................. 48/1
(58) Field of Classification Search .................. 48/1; 422/150
See application file for complete search history.

(56) References Cited

U.S. PATENT DOCUMENTS

| | | | | |
|---|---|---|---|---|
| 3,640,739 | A | * | 2/1972 | Bakker ..................... 501/129 |
| 4,765,964 | A | * | 8/1988 | Gravley et al. ............. 422/156 |
| 5,188,806 | A | * | 2/1993 | Kuehner et al. ............ 422/151 |
| 5,789,644 | A | | 8/1998 | Paessler et al. |
| 6,869,279 | B2 | * | 3/2005 | Bartenbach ................ 431/353 |

* cited by examiner

*Primary Examiner*—Glenn Caldarola
*Assistant Examiner*—Randy Boyer
(74) *Attorney, Agent, or Firm*—Oblon, Spivak, McClelland, Maier & Neustadt, L.L.P.

(57) ABSTRACT

The invention relates to a process for the scale-up of a reactor (1) having a supply of a reaction mixture via channels (2) of a burner block (3) to a reaction chamber (4), a high temperature reaction having a short residence time taking place in the reaction chamber (4) and the reaction mixture subsequently being rapidly cooled in a quench area (5). For a throughput enlargement the internal diameter of the reactor (1) is enlarged, the transition of the reaction chamber (4) to the quench area (5) being designed in the form of a gap, which is restricted to a width in the range from 2 to 200 mm.

Figure 1:
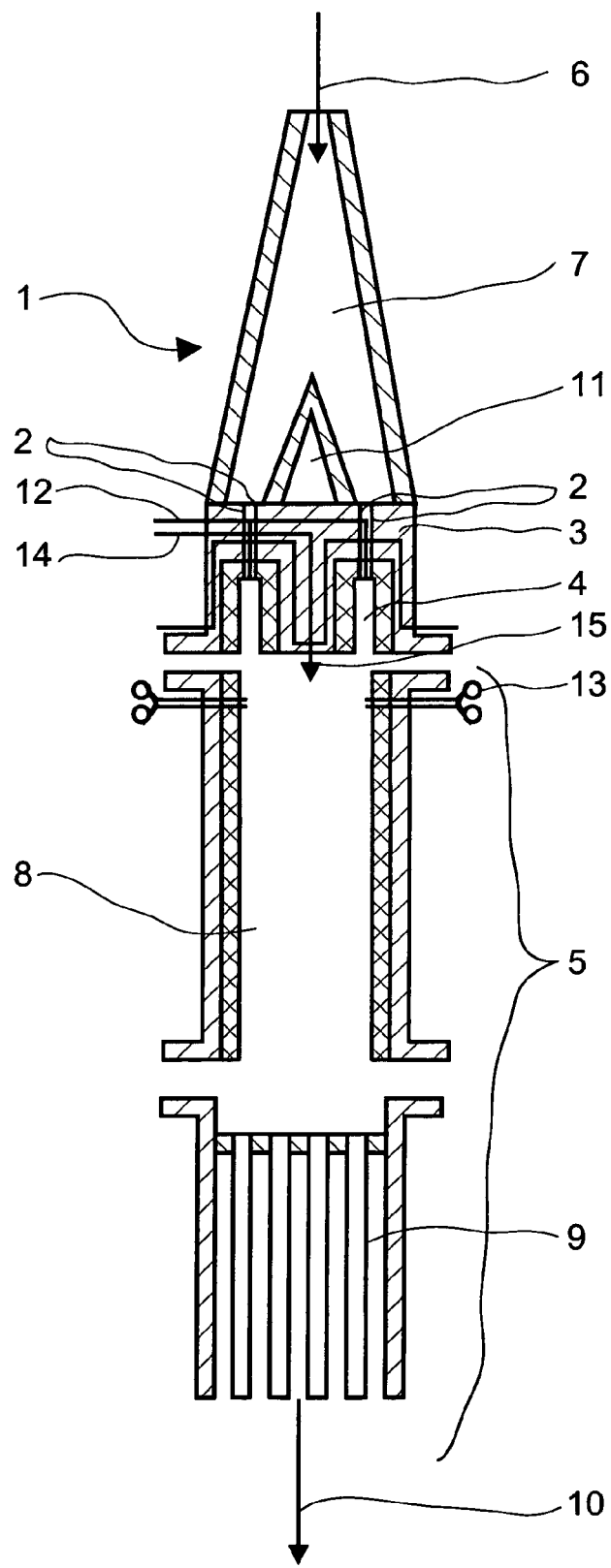

23 Claims, 4 Drawing Sheets x=550 mm   x=600 mm   x=650 mm   x=700 mm x=800 mm   x=900 mm   x=1000 mm   x=1200 mm x=1400 mm   x=1600 mm   x=1800 mm   x=2000 mm

T [K]

4.73e+02   6.23e+02   7.73e+02   9.23e+02   1.07e+03   1.22e+03   1.37e+03   1.52e+03   1.67e+03   1.82e+03   1.97e+03

PROCESS FOR THE SCALE-UP OF A REACTOR FOR CARRYING OUT A HIGH-TEMPERATURE REACTION, REACTOR AND USE

The invention relates to a process for the scale-up of a reactor, a reactor for carrying out a high-temperature reaction, and a use.

In the chemical industry, novel processes are as a rule first carried out and tested in the laboratory or on the pilot-plant scale. The transfer to the size of the production scale is not always without problems, since due to altered flow conduct of the individual substances behavior other than in the laboratory or pilot-plant experiments is frequently established. A further application area consists in the enlargement of already existing production plants for throughput enlargement.

High-temperature reactions are as a rule designated as reactions which take place at a temperature above 800° C. Short residence times are understood as meaning existing residence times in the millisecond range, in particular in the range from approximately 1 to 100 ms. Analogously, rapid cooling is defined as a cooling in the millisecond range, in particular in the range from approximately 1 to 100 ms.

Reactors in which a high-temperature reaction having a short residence time takes place and the reaction mixture is subsequently rapidly cooled in a quench area are employed, for example, for acetylene preparation.

The reactors for acetylene preparation employed on the present production scale are distinguished by a cylindrical geometry of the reaction chamber. A reactor of this type is described, for example, in DE-A 44 22 815. The premixed reaction substances are fed to a burner block without backmixing via a diffuser. The burner block has a circular cross-section and is permeated with channels. The reaction mixture is fed via the channels to a reaction chamber having a likewise circular cross-section. In the reaction chamber, the reaction mixture reacts with flame formation in an acetylene-forming partial oxidation reaction. To the reaction chamber is attached a quench container of relatively large cross-section, in which the quench nozzles are installed on one or more quench distributor rings, which atomize water or oil and jet into the reaction gas leaving the fire chamber approximately vertically to the main flow direction. The object of this direct water or oil quench is to cool the reaction mixture extremely rapidly so that subsequent reactions, such as, in particular, the breakdown of the acetylene formed, are frozen. The reach and distribution of the quench jets is ideally dimensioned here such that a temperature distribution which is as homogeneous as possible is achieved in a time which is as short as possible.

Enlargement of the reactor is problematical, since with increasing diameter of the cylindrical reaction chamber and of the cylindrical quench area the homogeneity of the quench action is more and more difficult to guarantee. This is because the penetration depth of the spray jets and the droplet size in the atomization are directly connected. This means that the small droplets necessary for rapid evaporation and thus a good quench action only achieve limited penetration depths, since the small droplets are prematurely deflected on account of the low impetus. Inhomogeneities in the quench action thereby occur, which favor the breakdown of the acetylene in the hotter streams. From this, the differences observed in the past in the acetylene yield between the smaller, older styles of construction of the reactors and the large reactors in use today, which produce a yield of approximately 25 tonnes per day, occur. The smaller burners achieve yields which are approximately 10%—relative to the yield of the large burner—higher.

It was the object of the invention to find a burner geometry which on scale enlargement causes no yield losses in order thereby with fewer production streams to manage with in each case larger units or in the case of existing larger units having a prespecified scale to achieve a yield and thus capacity increase.

The object is achieved by a process for the scale-up of a reactor having a supply of a reaction mixture via channels of a burner block to a reaction chamber, where in the reaction chamber a high-temperature reaction having a short residence time takes place and the reaction mixture is subsequently rapidly cooled in a quench area, characterized in that for a throughput enlargement the internal diameter of the reactor is enlarged, the transition from the reaction chamber to the quench area being designed in the form of a gap which is restricted to a width in the range from 2 to 200 mm.

Preferably, the transition from the reaction chamber to the quench area is restricted to a gap having a width in the range from 50 to 150 mm.

Using the solution according to the invention presented here, the disadvantages of the enlargement of the cylindrical cross section with respect to the realizable quench action are avoided by changing from the cylindrical geometry to a gap-like geometry. The gap is designed here such that heat dissipation is possible very effectively and homogeneously by direct spraying in of water from one or from both sides of the gap with small jet reaches and very fine sprays.

Preferably, this gap is designed as an annular gap, thus preceding and afterconnected plant parts, which as a rule have a cylindrical cross section, can be integrated more easily.

The invention also relates to a reactor having a supply of a reaction mixture via channels of a burner block to the reaction chamber, a high-temperature reaction having a short residence time taking place in the reaction chamber and the reaction mixture subsequently being rapidly cooled in a quench area, the reactor being characterized in that the transition of the reaction chamber to the quench area is designed in the form of a gap. Preferably, the gap is restricted to a width in the range from 2 to 200 mm, in particular in the range from 50 to 150 mm.

In a further preferred construction variant, the reaction chamber is also designed in the form of an annular gap.

The gap-like, preferably annular gap-like geometry of the transition from the reaction chamber to the quench chamber makes possible jetting in of the quench medium, for example water or oil, either from one side of the gap or from both sides of the gap.

The quench nozzles necessary for the jetting in can in this case be arranged in one or in a number of rows, for example staggered or linear.

Preferably, direct quenching is brought about in the quench area by introduction of a cooling medium via quench nozzles which are arranged radially or tangentially to the main flow direction of the reaction mixture in the reactor, in the case of a multistage introduction of cooling medium countercurrent positioning of the quench nozzles being preferred. In addition to a radial or tangential orientation of the quench nozzles to the main flow direction of the reaction mixture in the reactor, considered perpendicularly to the main flow direction in the cross-sectional plane, an orientation at an arbitrary angle to the main flow direction is also possible here.

Quench nozzles which can be employed here are pressure atomizers or atomizers which are assisted by an auxiliary medium, for example steam.

The rapid cooling of the reaction mixture in the quench area can preferably be brought about by direct or indirect quenching, i.e. in addition to the direct cooling indirect cooling in a heat exchanger is also possible by jetting in of a medium.

The direct quenching of the reaction mixture in the quench area can be brought about by a single- or multistage mixing of a cooling medium into the reaction mixture, preferably via one or more annular distributors.

It is possible to bring about the direct quenching of the reaction mixture in the quench area which is designed like an annular gap by direct mixing of cooling medium into the quench area which is designed like an annular gap from outside and/or from inside.

The quench area is preferably constructed aligning in the direction of the longitudinal axis of the reaction chamber, in particular as a gap, particularly preferably as an annular gap.

In order to insert the components designed like an annular gap into tubular connection cross sections, the channel designed like an annular gap should have a gradually widening hub closure, for example in the form of a rotation ellipsoid. The hub closure can be designed in solid form or preferably as an internally cooled hollow body. The hub closure is as far as possible designed to be flow separation-free.

Alternatively, an aerodynamic adaptation of the hub closure by spray or gas streams in the axial direction is conceivable.

The hub closure can be designed to be cooled or uncooled.

In the area of the burner block, the cross section which is like an annular gap can be designed with bores which are aligned in the longitudinal axis of the reaction chamber. The bores here are, for example, arranged in multiple concentric annular rings or in a hexagonal structure. In addition to the channels aligned parallel to the longitudinal axis of the reaction chamber, channels for the supply of the reaction mixture and channels for the supply of additional oxygen or of reaction auxiliaries can also be aligned at any desired angle to the longitudinal axis of the reaction chamber.

In addition to the preparation of acetylene, the principle of the annular gap geometry can also be transferred to the preparation of other products which need an intensive indirect or direct quench of the reaction.

In order to avoid coke and soot deposits, it is preferred to design all surfaces restricting the reaction chamber from a fire-resistant ceramic which is stable at reaction temperature, having an alumina content of at least 80%. In this context, the material of the parent substance to which the fire-resistant ceramic is to be applied is not essential. Preferably, in this context it is a metallic material.

Resistance of the ceramic to temperatures of over 800° C., in particular over 1300° C., occurring in the high temperature reactions is achieved by an alumina content of at least 80% by weight, preferably of at least 95% by weight and particularly preferably of at least 96% by weight.

The lining of the reaction chamber is carried out in a first embodiment variant by lining with the fire-resistant ceramic in the form of stones or blocks.

In a second embodiment variant, the fire-resistant ceramic is introduced into the reaction chamber in the form of a cast or tamped mass and subsequently compressed, dried and calcined there. In a preferred embodiment, the fire-resistant ceramic introduced into the reaction chamber as a cast or tamped mass is calcined by the high temperature reaction.

The fire-resistant ceramic with which the reaction chamber is lined advantageously has a thickness in the range from 7 to 30 cm, preferably a thickness in the range from 8 to 10 cm. Additionally, a back insulation of a ceramic having particularly good heat-insulating properties can be carried out.

An advantage of lining with a fire-resistant ceramic is that the lining has a therm insulating action. For this reason, the wall of the reaction chamber no longer needs to be cooled, which leads to a saving of cooling medium. A further advantage is that by means of sufficiently good fire-resistant insulation the soot deposition and thus the formation of coke can be prevented even under extreme conditions, i.e. at very high temperatures and heavy soot formation. By this means, the mechanical poker device and its laborious maintenance can be saved. Moreover, owing to the saving of the mechanical poker device, operating interruptions caused by poker error are saved. Finally, the material stress due to the erosive action of the coke which has been poked off on the afterconnected plant parts, such as pumps, heat exchangers and pipelines, is drastically reduced.

The invention also relates to the use of the process described above or of the reactor described above for the preparation of acetylene by partial oxidation of hydrocarbons using oxygen.

The invention is explained in greater detail below with the aid of a figure and of use examples.

Figure 2:
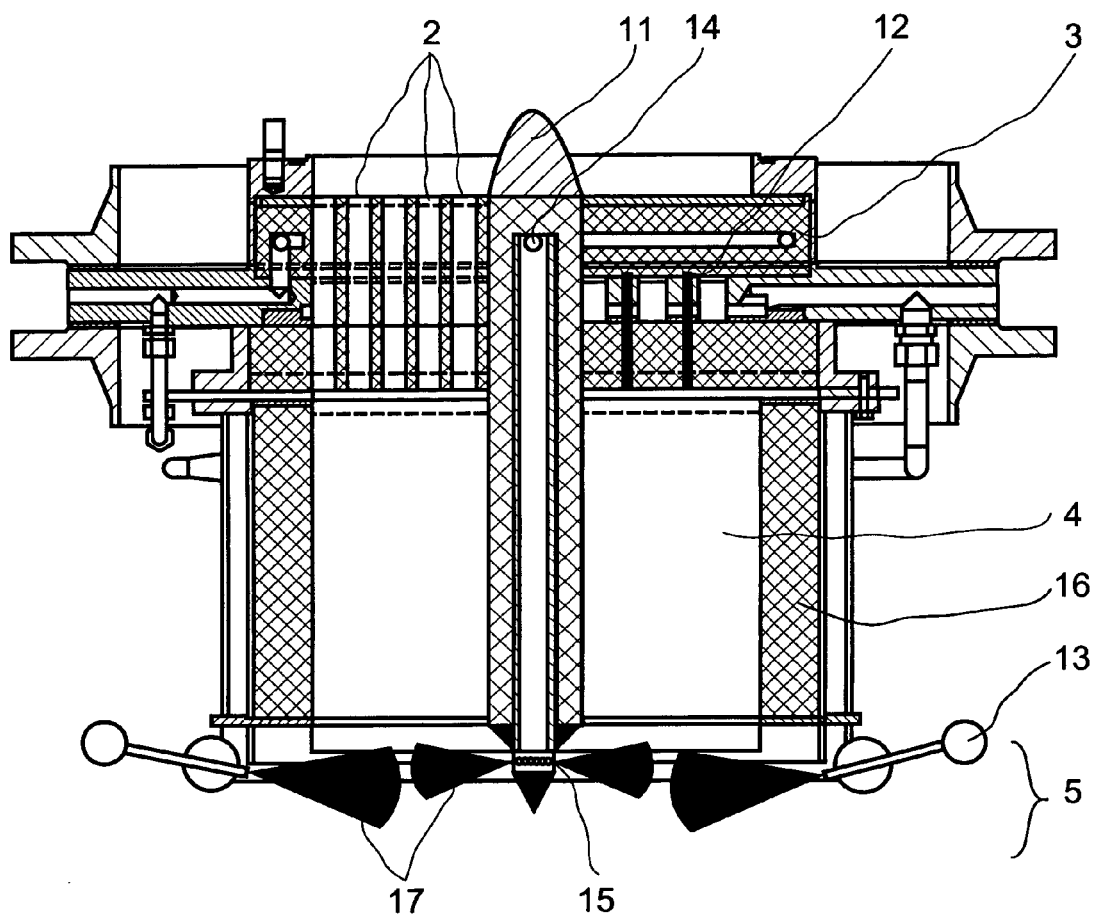
Figure 3:
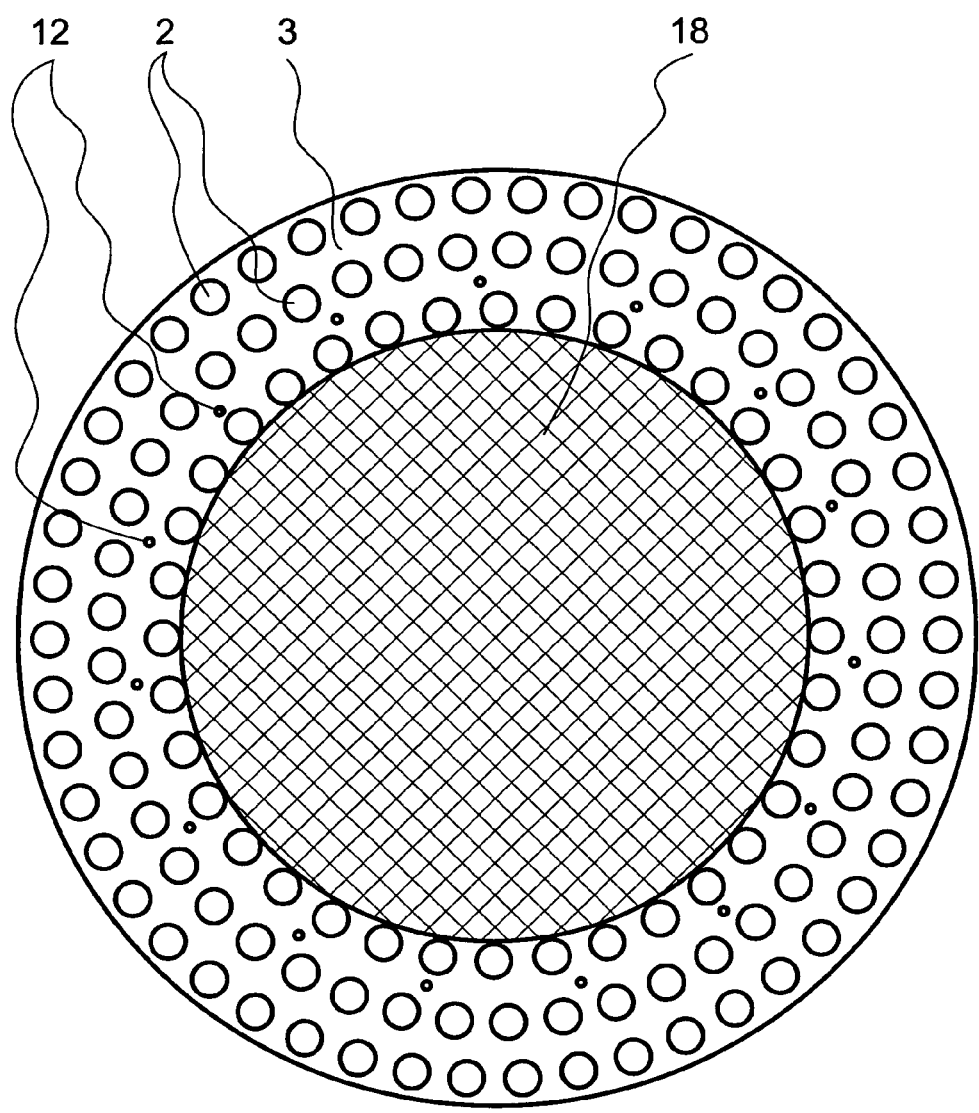
Figure 4:
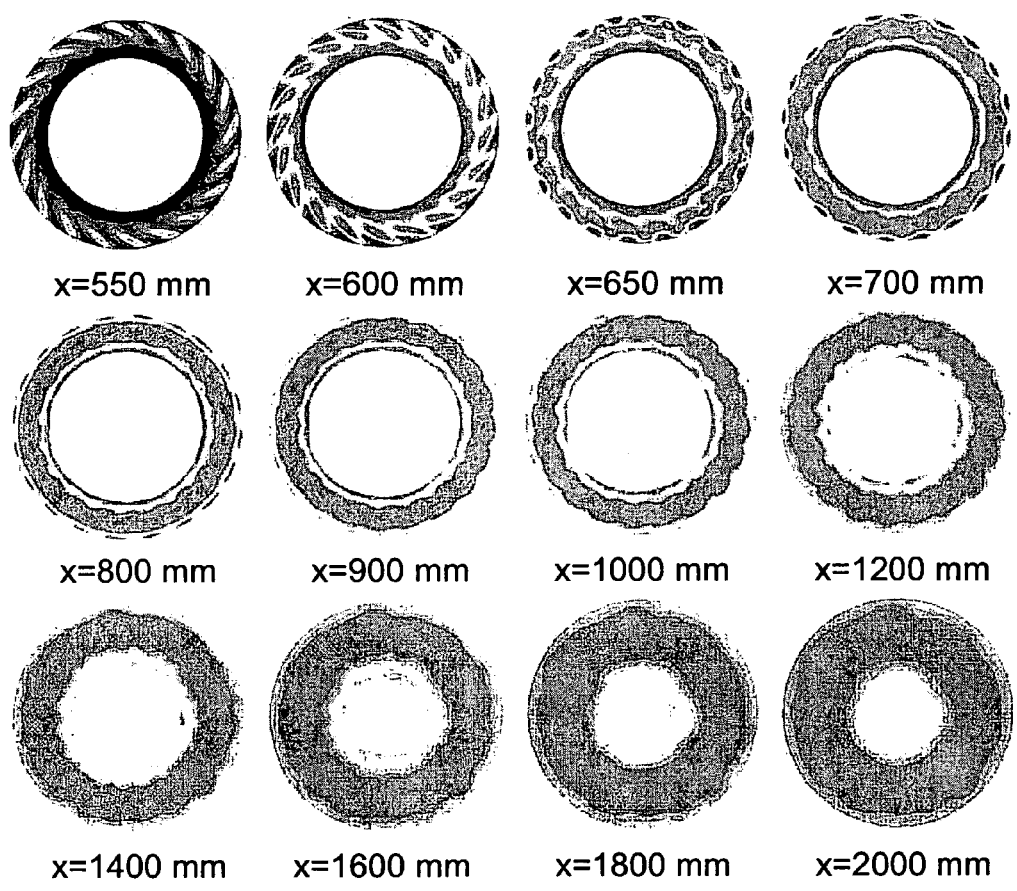
Figure 4:
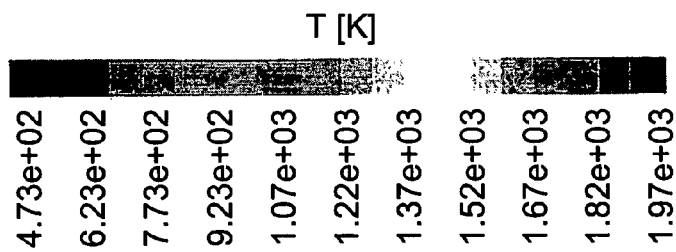

The following are shown in detail:

FIG. 1 an embodiment of a reactor designed according to the invention for acetylene preparation, FIG. 2 a section of a reactor, consisting of burner block, reaction chamber and quench area, FIG. 3 a cross section through a burner block which is designed like an annular gap, FIG. 4 temperature courses in a quench area designed like an annular gap having a hemiellipsoidal hub closure.

In the figures, identical reference symbols designate identical or corresponding features.

FIG. 1 shows a reactor 1 for acetylene preparation having a reaction chamber 4 designed like an annular gap. The reaction mixture is supplied to a reaction chamber 4 via channels 2 in a burner block 3 by a diffuser 7 via a delivery position 6. In the reaction chamber 4 a high temperature reaction having a short residence time takes place. The reaction mixture is subsequently rapidly cooled in a quench area 5. The mixture of reaction mixture and quench medium flows through a quench container 8 and arrives in a heat exchanger 9, which can be used for the utilization of the residual heat of the reaction mixture. From the heat exchanger 9, the reaction mixture arrives via an outlet 10 at further processes steps.

In order to guarantee an interference-free flow of the reaction mixture from the diffuser 7 into the channels 2 of the burner block 3, a hub closure 11 is situated in the diffuser 7. The hub closure 11 is designed as a cone or hemiellipsoid in a preferred embodiment variant.

The burner block 3 includes, in addition to the channels 2 for the reaction mixture which is supplied to the reaction chamber 4 through the diffuser 7, additional channels 12 for reaction auxiliaries or additional oxygen.

The quench medium, for example water or oil, is supplied via an annular quench distributor 13 having spray nozzles which are arranged annularly on the quench area 5. In addition to the quench nozzles, which are supplied via the external quench distributor 13, quench medium for cooling can also be sprayed into the quench area 5 via internal quench nozzles 15, which are supplied via a line 14.

To avoid baking on of coke and soot, the reaction chamber 4, the quench area 5 and the quench container 8 are lined with a fire-resistant ceramic 16.

FIG. 2 shows a section of a reactor 1, which includes the burner block 3, the reaction chamber 4 and the quench area 5. In contrast to FIG. 1, in FIG. 2 the hub closure 11 is not designed in the form of a cone, but in the form of a hemiellipsoid. Furthermore, FIG. 2 shows the spray jets 17 of the quench medium. The spray jets 17 are directed inwardly from the external quench nozzles, which are supplied via the quench distributor 13, and are directed outwardly from the internal quench nozzles 15, which are supplied via the line 14.

FIG. 3 is to be inferred as the top view of a burner block designed according to the invention. In the burner block 3, the channels 2 are arranged concentrically. In addition to the concentric arrangement, the channels could also be arranged hexagonally or in further arrangements. Additionally to the channels 2, the addition channels 12, which are here likewise arranged concentrically, can be identified. The internal area 18 of the burner block 3 is closed here by a fire-resistant ceramic. In addition to the completely closed construction variant, as is shown here, the internal area 18 of the burner block 3 can also contain the line 14 for the supply of the quench medium to the internal quench nozzles 15. Furthermore, the internal area 18 of the burner block 3 can also be designed as a hollow cylinder, for example for the purposes of cooling.

FIG. 4 shows the temperature courses along the quench area having a hemiellipsoidal hub closure calculated using the commercial software Fluent®.

In the position x=550 mm, quench medium is sprayed clockwise in a tangential direction into the quench area designed as an annular gap using annularly arranged quench nozzles. In the further course, it can be identified how the temperature in the area of the quench jets decreases. At x=650 mm, quench medium is sprayed tangentially counterclockwise into the quench area designed like an annular gap. The further pictures show how the temperature in the further course changes along the quench area. It can be clearly seen here that at a position x=1800 mm the direction of the spray jets can no longer be identified, but from outside to inside an annularly uniform temperature distribution is established. In this context, the temperature in the interior of the quench area still has a somewhat higher temperature than in the external area.

USE EXAMPLES

The influence of the gap geometry on the acetylene yield was investigated in a reactor designed according to FIG. 1. The outer diameter of the annular gap of the test apparatus employed was 720 mm, the internal diameter 480 mm. From this, a gap width of 120 mm resulted. The burner block employed in the test apparatus was designed according to FIG. 3 and had 126 bores distributed on 3 annular rings. For the cooling of the reaction mixture, 50 quench nozzles were attached distributed on the outer periphery of the quench area with water as a quench medium.

The reaction substances employed were oxygen and natural gas in a ratio of oxygen to natural gas of 0.59. The reaction substances were heated to 600° C. in a preliminary heating before they were supplied to the reaction chamber. The reaction mixture formed in the reaction contained a proportion of 9.4% of acetylene. In addition to the acetylene, 3.4% of carbon dioxide, 5.7% of methane, 24% of carbon monoxide and 56% of hydrogen are present. The yield of acetylene here is thus about 32.5% based on carbon.

In comparison with this, in a conventional burner with cylindrical geometry under identical boundary conditions, approximately 7.5-8.5% of acetylene is obtained in the reaction mixture. An example measurement in the running plant showed a proportion of 3.4% of carbon dioxide, 8.1% of acetylene, 5.5% of methane, 25.2% of carbon monoxide and 56.4% of hydrogen in the reaction mixture. The yield here is thus about 29.5% based on carbon.

LIST OF REFERENCE SYMBOLS

1 reactor
2 channels
3 burner block
4 reaction chamber
5 quench area
6 delivery position
7 diffuser
8 quench container
9 heat exchanger
10 outlet
11 hub closure
12 addition channels
13 quench distributor
14 line
15 internal quench nozzles
16 fire-resistant ceramic
17 spray jet
18 internal area

We claim:

1. A process for the scale-up of a reactor having a supply of a reaction mixture via channels of a burner block to a reaction chamber, a high temperature reaction having a short residence time taking place in the reaction chamber and the reaction mixture subsequently being rapidly cooled in a quench area, characterized in that for a throughput enlargement the internal diameter of the reactor is enlarged, the transition from the reaction chamber to the quench area being designed in the form of an annular gap which is restricted to a width in the range from 2 to 200 mm.

2. A process as claimed in claim 1, characterized in that the transition of the reaction chamber to the quench area is restricted to a gap having a width in the range from 50 to 150 mm.

3. A reactor having a supply of a reaction mixture via channels of a burner block to a reaction chamber, a high temperature reaction having a short residence time taking place in the reaction chamber and the reaction mixture subsequently being rapidly cooled in a quench area, characterized in that the transition of the reaction chamber to the quench area is designed in the form of an annular gap.

4. A reactor as claimed in claim 3, characterized in that the annular gap is restricted to a width in the range from 2 to 200 mm.

5. A reactor as claimed in claim 3, characterized in that the reaction chamber is designed in the form of an annular gap.

6. A reactor as claimed in claim 3, characterized in that the channels of the burner block are aligned in the longitudinal axis of the reaction chamber.

7. A reactor as claimed in claim 3, characterized in that some of the channels for the supply of the reaction mixture and/or channels for the supply of additional oxygen or of reaction auxiliaries are aligned at any desired angle to the longitudinal axis of the reaction chamber and otherwise the channels of the burner block are aligned in the longitudinal axis of the reaction chamber.

8. A reactor as claimed in claim 3, characterized in that the quench area is constructed aligning in the direction of the longitudinal axis of the reaction chamber.

9. A reactor as claimed in claim 3, characterized in that the rapid cooling of the reaction mixture in the quench area is brought about by direct or indirect quenching.

10. A reactor as claimed in claim 8, characterized in that the direct quenching of the reaction mixture in the quench area is brought about by single- or multistage mixing of a cooling medium into the reaction mixture.

11. A reactor as claimed in claim 9, characterized in that the direct quenching of the reaction medium in the quench area designed like an annular gap is brought about by direct mixing of cooling medium into the quench area designed like an annular gap from outside and/or from inside.

12. A reactor as claimed in claim 3, characterized in that in the quench area direct quenching is brought about by introducing a cooling medium via quench nozzles which are arranged radially or tangentially to the main flow direction of the reaction mixture in the reactor, where in the case of a multistage introduction of cooling medium a countercurrent positioning of the quench nozzles is preferred.

13. A reactor as claimed in claim 3, characterized in that all surfaces restricting the reaction chamber are formed of a fire-resistant ceramic which is stable at reaction temperature having an alumina content of at least 80% by weight.

14. A reactor as claimed in claim 13, characterized in that the alumina content of the fire-resistant ceramic is at least 95% by weight.

15. A reactor as claimed in claim 13, characterized in that the alumina content of the fire-resistant ceramic is at least 96% by weight.

16. A reactor as claimed in claim 13, characterized in that the fire-resistant ceramic is introduced into the reaction chamber in the form of stones or blocks or as a cast or tamped mass and subsequently compressed, dried and calcined.

17. A reactor as claimed in claim 16, characterized in that the cast or tamped mass is calcined by the high temperature reaction.

18. A reactor as claimed in claim 13, characterized in that the fire-resistant ceramic has a thickness in the range from 7 to 30 cm.

19. A reactor as claimed in claim 4, wherein the annular gap is restricted to a width in the range from 50 to 150 mm.

20. A reactor as claimed in claim 8, wherein a quench area is constructed as a gap.

21. A reactor as claimed in claim 20, wherein the gap has an annular shape.

22. A reactor as claimed in claim 10, wherein the direct quenching of the reaction mixture in the quench area is brought about by single- or multistage mixing of an cooling medium into the reaction mixture via one or more annular distributors.

23. A reactor as claimed in claim 18, wherein in the fire-resistant ceramic has a thickness in the range from 8 to 10 cm.

* * * * *